United States Patent [19]

Tummes et al.

[11] 3,993,695
[45] Nov. 23, 1976

[54] PROCESS FOR THE SEPARATION OF COBALT FROM PRIMARY PRODUCTS OF THE OXO-SYNTHESIS AND RECIRCULATION THEREOF TO THE SYNTHESIS STAGE

[75] Inventors: Hans Tummes, Oberhausen; Boy Cornils, Dinslaken; Josef Meis, Oberhausen; Dieter Ernst, Oberhausen; Hans-Joachim Tomuschat, Oberhausen, all of Germany

[73] Assignee: Ruhrchemie Aktiengesellschaft, Oberhausen, Germany

[22] Filed: Sept. 13, 1973

[21] Appl. No.: 397,045

[30] Foreign Application Priority Data
Sept. 16, 1972 Germany............................ 2245565

[52] U.S. Cl.......................................... 260/604 HF
[51] Int. Cl.².................................. C07C 45/04
[58] Field of Search............................. 260/604 HF

[56] References Cited
UNITED STATES PATENTS

| | | | |
|---|---|---|---|
| 2,683,177 | 7/1954 | Field............................ | 260/604 HF |
| 2,754,331 | 7/1956 | Smith........................... | 260/604 HF |
| 2,779,796 | 1/1957 | Munger......................... | 260/604 HF |

OTHER PUBLICATIONS

Morikawa, M., Chem. Abstracts, vol. 60, 14400, 1964.
Wender et al., Bur. of Mines Bull., No. 600, 1962.
Marko et al., Ber. vol. 94, pp. 847–850, 1961.
Marko et al., (I), Chem. Abstracts, vol. 55, 1961, 12131.
Morikawa, M., Bull. Chem. Soc. Japan, vol. 37, pp. 430–431.
Cotton et al., Advanced Inorganic Chemistry, 2nd Edit., 1966, p. 865.

Primary Examiner—James O. Thomas, Jr.
Assistant Examiner—W. B. Lone
Attorney, Agent, or Firm—Burgess, Dinklage & Sprung

[57] ABSTRACT

A process for the separation of cobalt from the primary products of the Oxo-synthesis, which products contain dissolved cobalt-carbonyl compounds, which comprises adjusting the sulfur content of the primary products so that the sulfur content is at least 15 mg/kg of primary product and subjecting the primary products containing sulfur in at least said amount to a steam treatment and separating precipitated cobalt therefrom.

16 Claims, 1 Drawing Figure

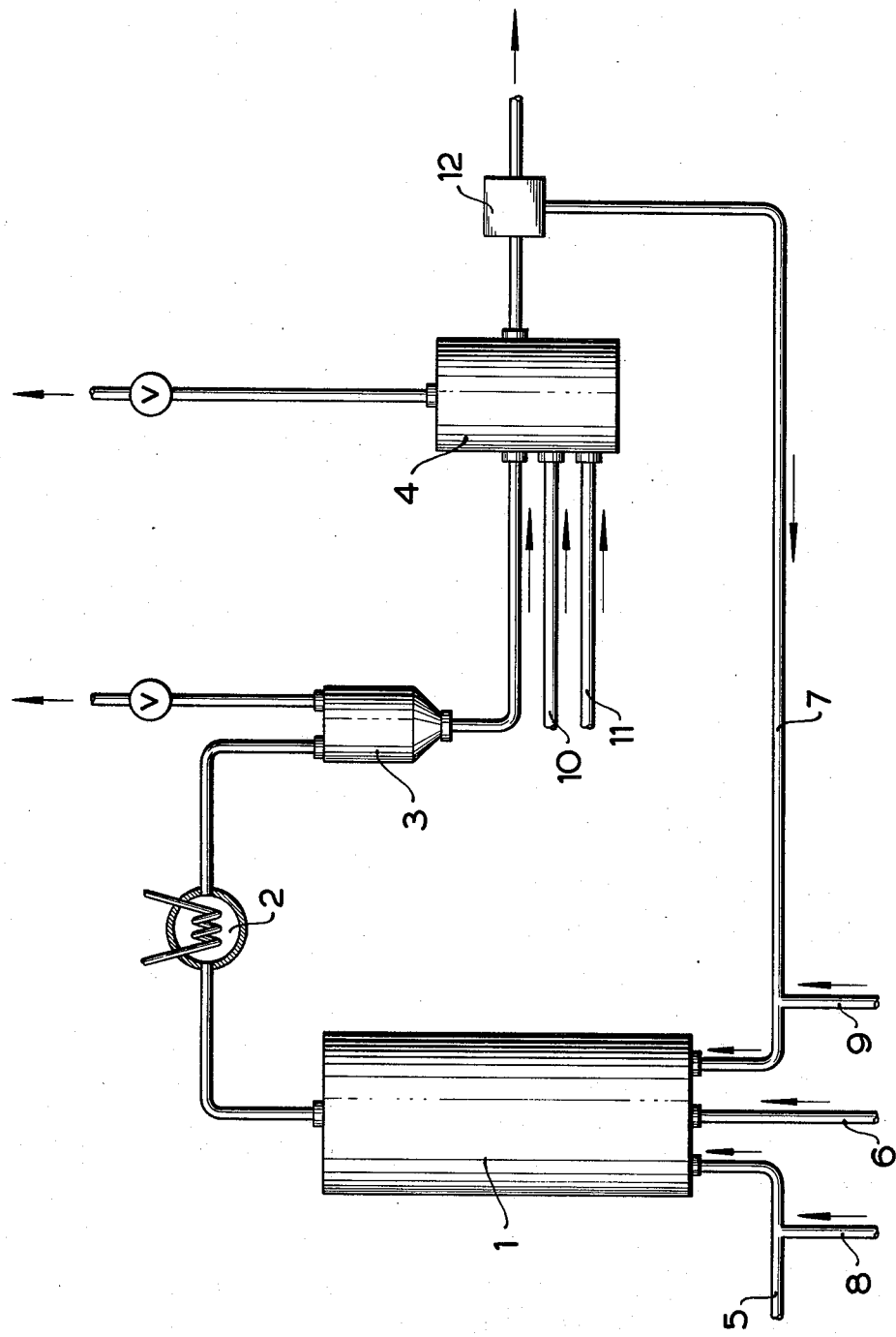

PROCESS FOR THE SEPARATION OF COBALT FROM PRIMARY PRODUCTS OF THE OXO-SYNTHESIS AND RECIRCULATION THEREOF TO THE SYNTHESIS STAGE

DISCUSSION OF THE PRIOR ART

In technical Oxo-processes known in the art, olefins are reacted with carbon monoxide and hydrogen in the presence of cobalt compounds at elevated temperatures and elevated pressures. The resulting raw products, known as "primary products," consisting preponderantly of primary aldehydes and alcohols contain the cobalt, used as catalyst in the form of dissolved cobalt-carbonyl compounds. These cobalt-carbonyl compounds considerably aggravate the further processing of the primary products, as for instance in their distillation and hydrogenation. Thus, these cobalt compounds must be eliminated in a separate "decobalting" stage.

It is essential for the economy of technical Oxo-processes to separate cobalt or cobalt compounds respectively in easily recoverable form from the organic reaction products and to recirculate the separated cobalt values to the hydroformylation stage without substantial loss and significant expenditure. In the numerous known processes for decobalting primary Oxo-products, the use of steam is preferred due to its economy and the further advantage that higher undesirable condensation products contained in the Oxo-products are at least partially decomposed. Dependent upon the prevailing reaction conditions, different decomposition products are obtained with the steam-treatment of the cobalt-carbonyl compounds, as, for instance, cobalt metal or cobalt hydroxide or, in the presence of acids, the cobalt salts of the latter.

From French Pat. No. 1,018,055 it is known to decompose cobalt-carbonyl compounds contained in the primary product of the Oxo-synthesis by means of steam to finely divided cobalt metal. The metal can be separated with the aid of mechanical separation devices from the organic phase containing the Oxo-synthesis products, and may be worked up to cobalt compounds in a consecutive stage, which are recirculated to the Oxo-process. In practicing the process it has been observed that in most cases only a part of the cobalt had been separated in the metallic state, while the remainder was dissolved in the aqueous phase. Furthermore, the known method does not always insure that the cobalt metal is obtained in easily removable form, as for instance, filterable condition.

German Offenlegungsschrift No. 1,937,662 describes the removal of the hydroformylation catalyst from raw Oxo-products by steam treatment, whereby the product to be treated must possess a sulfur content below 10 mg/kg, preferably below 2 mg/kg. In this event, a thorough sulfur removal of the starting olefins as well as of the synthesis gas is required. In the hereinbefore mentioned process, the entire cobalt contained in the Oxo-product is obtained in the form of an aqueous solution of cobalt salts, especially cobalt formate. However, if olefins having more than five carbon atoms are used as starting materials, the said procedure is not effective. In such known process, cobalt metal is not obtained, but cobalt hydroxide and/or basic cobalt formate is formed, which is separable with difficulty and highly inclined to form incrustations in the decobalting zone.

It is also known to introduce acids and/or oxidizing agents into the decobalting zone. The oxidation of the cobalt of the cobalt-carbonyl compounds contained in the raw Oxo-products is facilitated and the formation of the cobalt salts of the added acids is favored by such addition. It is preferred, to use acetic acid or formic acid and oxygen or air as oxidizing agents. If acid and water (formed by condensation of the added steam) are present in adequate amounts in the decobalting zone, cobalt is substantially obtained in the form of a dilute aqueous solution of a cobalt salt of the respective acid. Such solution can be recirculated to the hydroformylation stage only after further working up, which is generally encountered with involved operations.

The formation of highly diluted aqueous cobalt salt solutions, as for instance during steam treatment of raw Oxo-products low in or free of sulfur or during decobalting by means of steam in the presence of acids and/or oxidizing agents, is characterized by serious drawbacks. Since the Oxo-reaction products are only incompletely miscible with water, a heterogeneous liquid phase is formed in the Oxo-reactor at the recirculation of the aqueous cobalt salt solution, which leads to a decrease of the velocity of the conversion and may even cause a breakdown of the reaction. In order to prevent a decrease of the efficiency of the Oxo-reaction, the diluted aqueous cobalt salt solutions are either concentrated by evaporation of the main part of the water or the dissolved cobalt is precipitated and the resulting cobalt compound is recirculated to the Oxo-stage.

OBJECTS OF THE INVENTION

It is, therefore, an object of the invention to provide a method of separation of cobalt from the primary products of the Oxo-synthesis which secures an almost quantitative precipitation of the cobalt in solid form without formation of incrustations in the reactor, whereby the condition of the precipitated metal particles allows their easy separation from the liquid phase by conventional separation procedures. Finally, the separated cobalt should be recirculated as catalyst to the synthesis stage without the necessity of further working up operations.

SUMMARY OF THE INVENTION

Broadly, this invention contemplates a process for the separation of cobalt from the primary products of the Oxo-synthesis, said products comprising an aldehyde and an alcohol, said primary product containing dissolved cobalt-carbonyl compounds therein, which comprises adjusting the sulfur content of said primary products so that it is at least 15 mg sulfur per kg of primary product and contacting said primary product containing sulfur in said amount with steam. In accordance with the invention separated cobalt can be recirculated to the reaction zone of the Oxo-synthesis suitably as a suspension in distillate residue obtained by distilling an organic phase obtained from such steam treatment.

The present invention can be considered, therefore, as an improvement on the process of steam treating raw product from the Oxo-synthesis wherein either prior to or during the steam treatment of the primary products, the sulfur content thereof is adjusted to a critical minimum of at least 15 mg/kg of primary product. The sulfur content can be adjusted by adjusting the sulfur content of the reaction mixture of the Oxo-synthesis. Alternatively, it can be added to the zone of the steam treatment or the decobalting zone.

BRIEF DESCRIPTION OF DRAWING

The attached drawing is a flow diagram of the Oxo-process and the removal of cobalt catalyst therefrom and the recycle of such cobalt values to the Oxo-synthesis reaction zone.

DESCRIPTION OF PREFERRED EMBODIMENTS

The above objects are achieved, according to the invention, by a process for the separation of cobalt from the primary products of the Oxo-synthesis containing dissolved cobalt-carbonyl compounds by steam treatment of the primary products and the recirculation of the separated cobalt to the synthesis stage, whereby the sulfur content of the primary product is adjusted to at least 15 mg/kg of the primary product, optionally by addition of sulfur in suitable form before or during the steam treatment. The cobalt precipitated by the steam treatment is separated in known manner, suspended in a suitable organic solvent, especially in the distillation residues of the Oxo-process, and recirculated to the synthesis stage, if necessary after replenishing of cobalt losses.

Under direct influence of steam on the raw Oxo-product containing an adequate amount of sulfur, cobalt precipitates in the form of mechanically easily recoverable metal particles, without formation of incrustations in the reactor. Thereby the cobalt is so finely divided that it can be suspended in organic solvent, preferably in the distillation residues of the Oxo-synthesis without further processing and the resulting suspension can be recirculated, for instance, by means of pumps, to the Oxo-reactor. Since such suspensions having cobalt concentrations up to 20 to 30% can easily be prepared, they are especially suitable as catalysts in continuous cyclic processes and possess significant advantages in comparison to different systems. Besides the simplicity of their circulation, it is of particular advantage, that the amount of organic suspending liquid is considerably lower than the amount of water having to be introduced if aqueous solutions of cobalt salts or soaps respectively are circulated. Moreover, the organic suspension medium does in no manner impair the efficiency of the Oxo-reactor.

In order to obtain the cobalt metal as easily separable precipitate during the steam decobalting, without obstructions or incrustations caused by cobalt deposition, the sulfur content of raw Oxo-product must amount to more than 15 mg/kg. Preferably, the sulfur content is at least 20 mg/kg primary product. Especially at a concentration between about 3 to 10 mg S/kg raw Oxo-product, the precipitated cobalt metal particles tend to form incrustations, while this drawback is no more observed at sulfur contents above 15 mg S/kg of the raw Oxo-product.

The sulfur content according to the invention is adjusted by addition of elemental sulfur (flowers of sulfur) or of sulfides to raw Oxo-products free of or low in sulfur. The term "sulfides" comprises inorganic sulfides, as for instance, hydrogen sulfide, carbon oxysulfide, ammonium sulfide, alkali sulfides, alkaline earth metal sulfides, cobalt sulfide, as well as organic sulfur compounds, as for instance, mercaptans, mercaptides, thioethers, carbon disulfide.

Sulfur or sulfur compounds respectively can be introduced into the Oxo-reactor during the hydroformylation stage as well as the decobalting zone. It is of little consequence if the sulfur or the sulfur compounds are added alone or together with the starting materials, as for instance synthesis gas, olefins, catalyst or steam, into the system, but normal care should be taken that they are quickly and finely distributed within the reaction vessel.

According to a preferred embodiment of the process according to the invention, elemental sulfur is used in the form of flowers of sulfur and introduced into the synthesis stage in suspension together with the recirculated cobalt metal precipitate. This method of sulfur doping is characterized by high efficiency and is easily operable, since only a corresponding amount of flowers of sulfur has to be mixed by stirring with the cobalt suspension.

Since the decomposition of the cobalt-carbonyl compounds proceeds in the decobalting stage, sulfur or sulfur compounds can also be introduced, as hereinbefore stated, into the decobalting zone. Owing to the presence of water, formed by condensation of the steam used for the decobalting procedure, water soluble sulfur compounds, as, for instance, hydrogen sulfide, ammonium sulfide or alkali sulfides, are in this case employed. However, oil soluble sulfur compounds can also be introduced into the decobalting zone, while otherwise water soluble sulfides can be introduced into the synthesis stage.

The steam treatment of the primary Oxo-products is carried out in conventional manner by introducing steam at temperatures between about 100° to 220° C, preferably between 130° and 180° C and pressures between about 5 and 30 atm, preferably between 10 and 20 atm. Cobalt precipitated in finely divided form can be separated by filtration, decantation or centrifuging from the liquid phase.

By circulating the cobalt catalyst on basis of cobalt metal, the main part of the added sulfur remains in the form of cobalt sulfide in the circulating catalyst. Therefore, the required sulfur concentration of the system can be maintained if only the amount of sulfur lost by passing over from the circulating catalyst system to the organic product or to the aqueous phase during the steam treatment is replenished. The upper limit of the sulfur concentration in the raw Oxo-product depends upon the impairment of the catalytic activity of the cobalt catalyst. Much more than 500 mg S/kg raw Oxo-product are allowable, even more than 1000 mg/kg if the sulfur contained in the Oxo-product is present in the form of cobalt sulfide or of cobalt-sulfocarbonyls. Even at sulfur amounts of the hereinbefore stated order of magnitude, the resulting raw Oxo-products are surprisingly of equivalent quality as those obtained by Oxo-synthesis in absence of sulfur.

The process according to the invention is not inherent to certain starting olefins but may generally be used for the conversion of any olefin, only the sulfur content in the primary product, determined by the initial sulfur content of the reactant (olefin, synthesis gas) and the added sulfur, is decisive. Thus, the novel process is well suited for the conversion of sulfur free starting materials especially sulfur free synthesis gas, as well as for the conversion of starting materials, whose sulfur content leads to the hereinbefore stated unfavorable sulfur content of the resulting Oxo-product of 3 to 14 mg/kg. The novel process is especially well suited for the conversion of propylene, butenes, heptenes, octenes, tri- or tetrapropylene and different polymeric olefins, olefins produced by thermal or catalytic cracking of paraffins as well as olefins obtained by the "growth-reaction" of Ziegler.

Since the addition of sulfur or sulfur compounds influences only the decobalting procedure, but does not injure the proper hydroformylation reaction, the process according to the invention may be used for any Oxo-process, at which the cobalt-carbonyl compounds are decomposed by means of steam. No additional expenditure impairing the economy of the Oxo-process, as for instance, refining of the reactants, addition of acids and/or oxidizing agents as well as working up of diluted cobalt salt solutions is required.

EXAMPLES

In a semi-technical testing device according to the attached drawing, comprising an Oxo-reactor 1, a product condenser 2 and a gas separator 3 a cobalt carbonyl containing raw Oxo-product (primary product) was prepared in known manner. Synthesis gas was introduced through line 5, olefin through line 6 and Oxo-catalyst through line 7 into reactor 1. Sulfur or sulfur compounds respectively are added in defined amounts, controlled by a separate regulating device through line 8 to the synthesis gas, through line 9 to the catalyst and through line 11 to a decobalting zone 4.

The raw Oxo-product exiting from gas separator 3 representing a mixture of aldehydes, alcohols, esters and further by products, containing cobalt carbonyl and, owing to the respective reaction conditions, more or less sulfur, was added in the decobalting zone 4 with steam introduced through line 10. The decobalted hydroformylation mixture leaving decobalting zone 4 comprises three phases, an organic phase ("raw aldehyde") an aqueous phase containing dissolved cobalt and a solid phase consisting of finely divided cobalt precipitate or a two-phase system of raw aldehyde/water. Both complex mixtures can be separated by suitable devices 12.

Temperatures between 120° and 180° C and pressures between 200 and 350 atm generally prevail in the synthesis stage, the amount of cobalt, depending on the olefin, ranges preferably between 0.1 and 1.0% by weight.

The temperatures in the steam-treatment zone range between 50° and 180° C, preferably between 120° and 160° C; the pressures range between 5 and 30 atm, preferably between 10 and 20 atm.

The test results obtained with the process according to the invention are listed in the attached table. In said tests, the cobalt- and sulfur-contents of the raw Oxo-product exiting from high pressure separator 3 and the cobalt contents of the several phases of the complex system exiting from the decobalting zone 4 were determined. The experimental data obtained at the several tests as well as the corresponding reaction conditions are set forth in the table. By determination of the amount of the single phases, the amount of dissolved cobalt in the raw aldehyde and the water phase respectively as well as the yield of solid cobalt values were evaluated. Cobalt metal as well as cobalt compounds obtained after the demetallizing treatment were continuously recirculated to the reactor.

Table

| Example | starting-olefin | conversion in the synthesis stage % | decobalting stage temp. °C | pressure atm. | added sulfur compound |
|---|---|---|---|---|---|
| 1 | propylene | 99 | 150 | 12 | — |
| 2 | propylene | 99 | 150 | 12 | COS/H$_2$S in the synthesis gas |
| 3 | propylene | 98.5 | 150 | 12 | COS/H$_2$S in the synthesis gas |
| 4 | propylene | 98.4 | 150 | 12 | flowers of sulfur in the starting catalyst |
| 5 | propylene | 98.5 | 150 | 12 | CoS in the starting catalyst |
| 6 | propylene | 98.7 | 150 | 12 | CS$_2$ in the starting catalyst |
| 7 | propylene | 98.4 | 150 | 12 | H$_2$S in the starting gas |
| 8 | propylene | 98.7 | 150 | 12 | aqueous (NH$_4$)$_2$S in the decobalting zone |
| 9 | propylene | 97.5 | 150 | 12 | CoS in the starting catalyst |
| 10 | diisobutylene | 96.0 | 180 | 20 | — |
| 11 | diisobutylene | 95.0 | 180 | 20 | aqueous (NH$_4$)$_2$S in the decobalting zone |
| 12 | α-olefin C$_8$—C$_{10}$ mixture | 97.0 | 180 | 20 | — |
| 13 | α-olefin C$_8$—C$_{10}$ mixture | 95.5 | 180 | 20 | COS/H$_2$S in the synthesis gas |
| 14 | α-olefin C$_8$—C$_{10}$ mixture | 95.6 | 180 | 20 | flowers of sulfur in the starting catalyst |
| 15 | isobutene | 97.5 | 160 | 15 | aqueous Na$_2$S in the decobalting zone |
| 16 | isobutene | 97.0 | 160 | 15 | aqueous Na$_2$S in the decobalting zone |
| 17 | isobutene | 96.0 | 160 | 15 | aqueous Ca(HS)$_2$-solution in the decobalting zone |
| 18 | isobutene | 97.0 | 160 | 15 | —SH in the starting catalyst |
| 19 | isobutene | 97.5 | 160 | 15 | 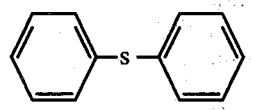 in the starting catalyst |
| 20 | isobutene | 97.0 | 160 | 15 | —S Na in the decobalting zone |

| Example | raw Oxo-product (primary product) Co g/kg | raw Oxo-product (primary product) S mg/kg | decobalted raw Oxo-product mg Co/l | cobalt dissolved in the organic phase | cobalt dissolved in H₂O | % of Co-slurry | Co as Co-hydroxide | notes |
|---|---|---|---|---|---|---|---|---|
| 1 | 2.42 | <1 | 80 | 3.2 | 96.8 | — | — | |
| 2 | 2.40 | 8 | 10 | 0.4 | 32.0 | 67.6 | — | Co-incrustations in the decobalting zone |
| 3 | 2.35 | 20 | 5 | 0.2 | 31.6 | 68.2 | — | |
| 4 | 2.40 | 59 | 5 | 0.2 | 18.3 | 81.5 | — | |
| 5 | 2.43 | 78 | 5 | 0.2 | 18.2 | 81.6 | — | |
| 6 | 2.38 | 64 | 8 | 0.3 | 13.7 | 86.0 | — | |
| 7 | 2.41 | 50 | 5 | 0.2 | 13.9 | 85.9 | — | |
| 8 | 2.45 | 18 | 5 | 0.2 | 11.8 | 88.0 | — | |
| 9 | 2.40 | 300 | <5 | 0.1 | 10.0 | 89.9 | — | |
| 10 | 3.10 | <1 | 90 | 3.6 | 35.0 | 0.4 | 61.0 | |
| 11 | 3.17 | 10 | 15 | 0.6 | 22.0 | 76.0 | 1.4 | Co-incrustations in the decobalting zone |
| 12 | 3.21 | <1 | 140 | 5.8 | 34.2 | 2.0 | 58.0 | |
| 13 | 3.20 | 60 | 10 | 0.4 | 13.2 | 86.0 | 0.4 | |
| 14 | 3.22 | 55 | 5 | 0.2 | 12.0 | 87.6 | 0.2 | |
| 15 | 2,8 | 1 | 110 | 9,6 | 90,2 | 0,2 | — | |
| 16 | 2,9 | 22 | 6 | 0,2 | 12,4 | 87,4 | — | |
| 17 | 3,0 | 45 | 5 | 0,1 | 11,2 | 88,7 | — | |
| 18 | 2,7 | 40 | 6 | 0,2 | 14,1 | 85,7 | — | |
| 19 | 3,1 | 52 | 7 | 0,1 | 13,5 | 86,4 | — | |
| 20 | 3,0 | 35 | 8 | 0,1 | 12,7 | 87,2 | — | |

The examples hereinbefore set forth show the following.

The hydroformylation of olefins and the consecutive decobalting of the reaction mixture exiting from the Oxo-reactor leads at sulfur contents below 1 mg/kg and in the absence of acids and/or oxidizing agents to residual cobalt contents of 80 to 140 mg/l in the organic phase of the valuable products (Examples 1, 10 and 12). Under these decobalting conditions, the main part of the cobalt used as catalyst is obtained, as cobalt salt dissolved in water, if propylene is used as starting olefin and as cobalt hydroxide, if higher olefins are used as starting material.

By addition of small amounts of sulfur the residual cobalt content of the organic phase can be decreased to less than 10 mg/l, while simultaneously the amount of suspended cobalt metal in the Oxo-raw product after the decobalting stage increases.

At sulfur contents of about 3 up to 14 ppm, however, the cobalt is obtained not only suspended in the liquid phase, but obnoxious cobalt incrustations at the walls of the decobalting device are formed (Examples 2 and 11).

At a sulfur content of more than 15 ppm S/kg of the raw Oxo-product, a good decobalting with high yields of cobalt metal is obtained, without formation of cobalt incrustations in the decobalting stage. Especially well suited are, for instance, the following sulfur compounds: COS or H₂S added with the gas or introduced into the decobalting zone (Examples 2, 3 and 7 and 13), flowers of sulfur in the cobalt catalyst (Examples 4 and 14), cobalt sulfide in the starting catalyst (Examples 5 and 9), carbon disulfide (Example 6) or aqueous ammonium sulfide solution (Examples 8 and 11).

Oxo-Synthesis or hydroformylation is the reaction of an unsaturated compound (or a saturated compound which may generate an unsaturated compound) with carbon monoxide and hydrogen to yield an aldehyde. Under suitable reaction conditions the aldehydes formed may partly be hydrogenated to the corresponding alcohols by the hydrogen present. There are processes known in which this fact is used to make alcohols in a single stage. However, in most of the operating plants the aldehydes are converted into alcohols in a second stage. Hydroformylation is often accompanied by sequential or side reactions. Frequently found as sequential reactions are aldol condensation and acetal formation, Tishenko type reactions as well as oligomerization and polymerization. The formation of formate esters is also frequently encountered, especially at higher temperatures as well as ketone formation (see Jürgen Falbe "Carbon Monoxide in Organic Synthesis" Translated by Charles R. Adams, Springer-Verlag Berlin . Heidelberg . New York 1970, chapter I "The Hydroformylation Reaction Oxo Reaction/Roelen Reaction").

What is claimed is:

1. In a process for the preparation of a primary product consisting of at least one aldehyde by the Oxo-process wherein an olefin, carbon monoxide and hydrogen are reacted under Oxo-process conditions in the presence of a dissolved cobalt carbonyl compound and the resultant reaction mixture is subjected to a steam treatment at a temperature in the range of 100° to 220° C and pressure of between 5 and 30 atmospheres to effect separation of cobalt from said primary products, the improvement for inhibiting precipitation of cobalt compound of the walls of the reactor prior to said steam treatment which consist of adding a source of sulfur to the sulfur content of the reaction mixture prior to completion of steam treatment so that there is at least 15 mgs. sulfur per kilogram of primary product in the reaction mixture being steam treated.

2. A process according to claim 1 wherein sulfur is added to the primary products employing a sulfur compound.

3. A process according to claim 1 wherein sulfur is added to the primary products in the form of elemental sulfur.

4. A process according to claim 1 wherein the sulfur content of the primary products is adjusted by introducing sulfur into the reaction mixture of the Oxo-process.

5. A process according to claim 1 wherein the separated precipitated cobalt is recirculated to the reaction zone of the Oxo-process.

6. A process according to claim 5 wherein an organic phase is recovered from the products of the steam treatment; said organic phase is subjected to distillation to remove aldehyde therefrom, the distillation residue is admixed with the separated cobalt and the mixture is recycled to the reaction zone of the Oxo-process.

7. A process according to claim 3 wherein any sulfur added to adjust the sulfur content is added in the form of flowers of sulfur.

8. A process according to claim 1 wherein sulfur or a compound thereof is added during the steam treatment.

9. A process according to claim 2 wherein the sulfur compound employed is an inorganic sulfur compound.

10. A process according to claim 2 wherein the sulfur compound employed is an organic sulfur compound.

11. A process according to claim 1 wherein the steam treatment of the Oxo-synthesis product is effected at temperatures in the range of 100° to 220° C and at a pressure of between 5 and 30 atm.

12. A process according to claim 11 wherein the steam treatment is effected at a temperature between 130° and 180° C and at a pressure between 10 and 20 atm.

13. A process according to claim 1 wherein the product obtained from the steam treatment is subjected to centrifuging and three phases are recovered, said phases being a substantially cobalt-free organic phase, an aqueous phase containing cobalt salts and a solid phase comprising finely divided cobalt metal.

14. A process according to claim 13 wherein to the aqueous phase containing cobalt salts there is added an aqueous solution of an alkali hydroxide or an alkali carbonate whereby to precipitate a cobalt compound, the cobalt compound is separated from the aqueous phase and the so-separated cobalt compound is recycled together with cobalt containing solids to the reaction zone of the Oxo-synthesis.

15. A process according to claim 1 wherein the sulfur content of the primary products is between 1 and 1000 mg/kg of primary product.

16. A process according to claim 15 wherein the sulfur is introduced in the form of hydrogen sulfide, carbon oxysulfide, ammonium sulfide, an alkali sulfide, an alkaline earth metal sulfide, a cobalt sulfide, an element sulfur, a mercaptan, a mercaptide, a thioether, or carbon disulfide.

* * * * *